(12) United States Patent
Lee

(10) Patent No.: US 8,117,176 B2
(45) Date of Patent: Feb. 14, 2012

(54) FOOD NUTRITION MANAGEMENT SYSTEM AND METHOD

(76) Inventor: Ronald Lee, Sindian (TW)

( * ) Notice: Subject to any disclaimer, the term of this patent is extended or adjusted under 35 U.S.C. 154(b) by 529 days.

(21) Appl. No.: 12/379,133

(22) Filed: Feb. 13, 2009

(65) Prior Publication Data

US 2010/0076942 A1 Mar. 25, 2010

(30) Foreign Application Priority Data

Sep. 10, 2008 (TW) .............................. 97134687 A

(51) Int. Cl.
*G06F 7/00* (2006.01)
(52) U.S. Cl. ....................................................... 707/705
(58) Field of Classification Search .................. 707/705, 707/771
See application file for complete search history.

(56) References Cited

U.S. PATENT DOCUMENTS

| | | | | |
|---|---|---|---|---|
| 6,460,055 | B1 * | 10/2002 | Midgley et al. ................ 707/640 |
| 7,020,774 | B1 * | 3/2006 | Cornuejols et al. ........... 713/176 |
| 7,340,439 | B2 * | 3/2008 | Burger et al. .................... 705/65 |
| 2007/0276823 | A1 * | 11/2007 | Borden et al. ................. 707/723 |
| 2008/0313616 | A1 * | 12/2008 | Malcolm ........................ 717/127 |
| 2009/0094229 | A1 * | 4/2009 | Ferrel et al. ................... 707/723 |

* cited by examiner

*Primary Examiner* — Shahid Alam
*Assistant Examiner* — Donald Lawson
(74) *Attorney, Agent, or Firm* — Bacon & Thomas, PLLC

(57) ABSTRACT

A food nutrition management system provides a portable electronic device to a user for inputting a personal data and special codes. The personal data and the special codes are received by a register and management unit for further registering at a database. The database is searched for a food nutrition component table corresponding to a special code. The food nutrition component table searched is transmitted for displaying on a display unit, stored in the database when a store instruction is input through the portable device, and analyzed and compared with a suggestion of daily ingestion amounts per person for a variety of nutrition when an inquiry instruction is input. The portable electronic device displays current and past ingestion amounts for the variety of nutrition and notices the user of which nutrition is insufficient or surplus and of the possible diseases and symptoms.

19 Claims, 2 Drawing Sheets

FOOD NUTRITION MANAGEMENT SYSTEM AND METHOD

BACKGROUND OF THE INVENTION

1. Field of the Invention

The present invention relates to the technical field of food nutrition management and, more particularly, to a food nutrition management system and method suitable for individuals and food industries.

2. Description of Related Art

Generally, consumers are unaware of how many calories and how much nutrition are actually ingested, and so the absorbed nutrition can be unbalanced. A food nutrition component table is labeled on the packaging of various foods and drinks sold in the shops. However, the food nutrition component table cannot be effectively used as a reference of daily nutrition planning or purchase for the consumers since the nutrition amount of each unit labeled by the manufacturers is different and the consumers cannot manipulate the daily nutrition ingestion amounts per person easily. For the elder, women and children, some nutrition lacks or surpluses normally lead to certain diseases. Further, most restaurants or people at home have no nutrition details on cooking for the nutrition management.

Therefore, it is desirable to provide an improved food nutrition management method and system to mitigate and/or obviate the aforementioned problems.

SUMMARY OF THE INVENTION

The object of the present invention is to provide a food nutrition management method and system, which can provide the daily nutrition ingestion calculation to a consumer and the food nutrition calculation and management to a food dealer.

To achieve the object, a food nutrition management method is provided, which is applied in a food nutrition management system including a portable electronic device, a transmitting unit, a database, an operation unit, a code generator, an analyzer and a register and management unit. The method includes: receiving a personal data through the transmitting unit from the portable electronic device to the register and management unit, storing and registering the personal data to the database; externally inputting a special code through the portable electronic device, sending the special code through the transmitting unit to the register and management unit for being recorded; using the register and management unit to extract the special code and corresponding food nutrition component table from the database and to send the corresponding food nutrition component table through the transmitting unit to the portable electronic device for display; using the register and management unit to store the corresponding food nutrition component table in the database when a store instruction is input through the portable electronic device; using the analyzer to extract the corresponding food nutrition component table from the database, compare the corresponding food nutrition component table with a suggestion of daily ingestion amounts per person for a variety of nutrition, and send a comparison result to the portable electronic device when an inquiry instruction is input through the portable electronic device; and using the portable electronic device to display current and past ingestion amounts for the variety of nutrition, send a notice of which nutrition is insufficient or surplus, and provide possible diseases and symptoms corresponding to the nutrition insufficient or surplus.

According to the personal data including account numbers, passwords, heights, weights, sexes, exercise amounts and diseases, the suggestion of daily ingestion amounts per person is produced by the operation unit. Thus, the daily ingestion amounts per person are effectively recorded, and the purpose of personal health management is achieved.

To achieve the object, a food nutrition management system is also provided. The system includes a portable electronic device, a transmitting unit, a database, an operation unit, a code generator, an analyzer and a register and management unit. The portable electronic device is a mobile phone, personal digital assistant (PDA), handheld game machine, laptop/notebook computer, game host or network server for receiving data. The data includes one or more selected from personal data, cooking materials, food nutrition component tables, 1D barcodes, 2D barcodes and 3D barcodes. The personal data includes one or more selected from account numbers, passwords, heights, weights, sexes, exercise amounts and diseases. The transmitting unit is a network for transmitting the data received by an input unit of the portable electronic device. The database is implemented in the mobile phone, personal digital assistant (PDA), handheld game machine, laptop/notebook computer, game host or network server for storing nutrition components of a plurality of cooking materials, food nutrition component tables and special codes for a plurality of products, restaurant data, and records of personal data and daily nutrition ingestion. The restaurant data includes one or more selected from phone numbers, addresses, open hours and food information. The operation unit accesses the database for calculating a total of nutrition components of cooking materials. The code generator generates the special codes of the products. The analyzer extracts the food nutrition component tables from the database for analyzing and comparing them with a suggestion of daily ingestion amounts per person for a variety of nutrition. The portable electronic device includes a display unit to display a menu and corresponding food nutrition component tables. The register and management unit receives the data and special code transmitted by the transmitting unit for being recorded.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
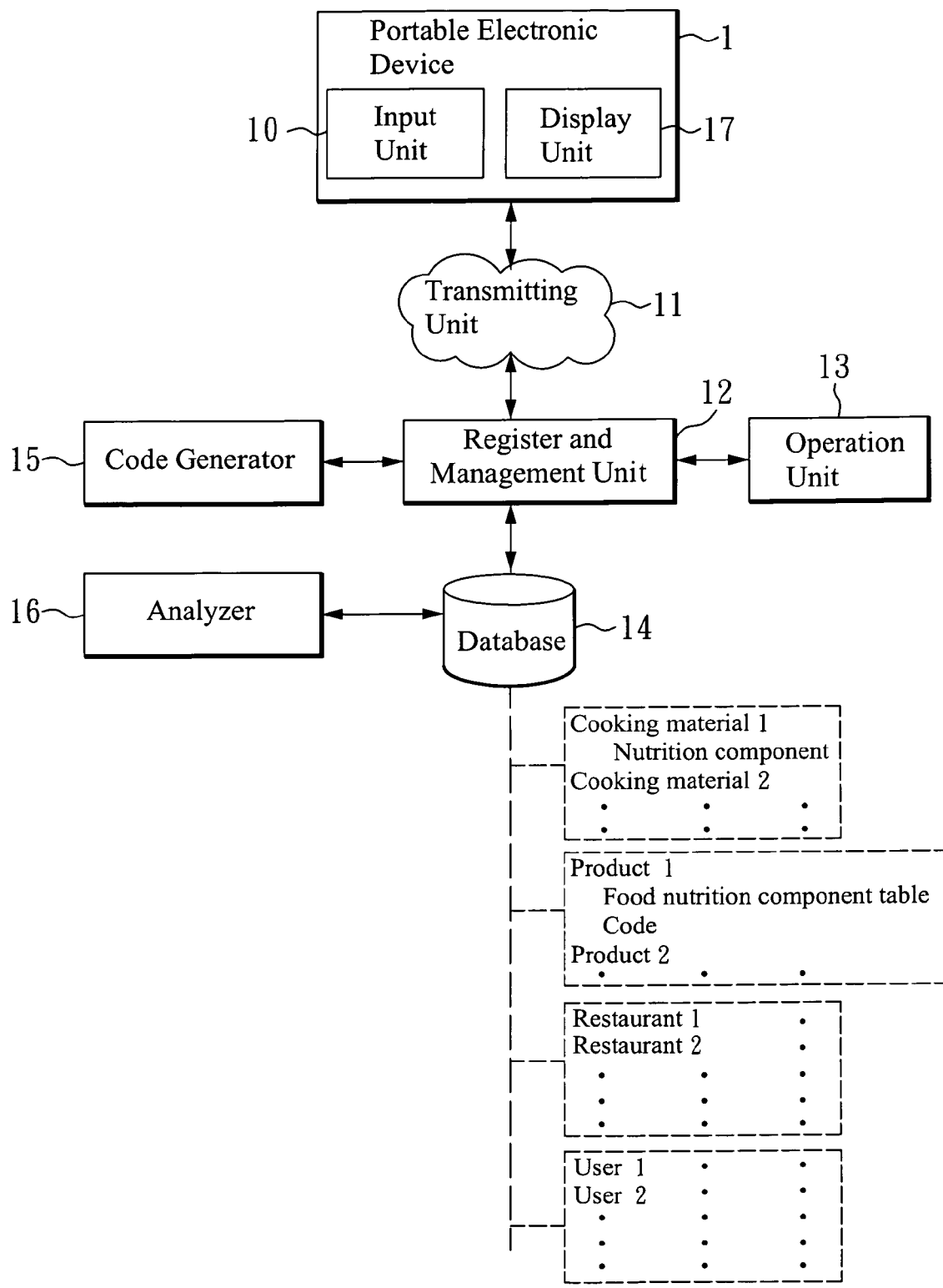
FIG. 1 is a schematic diagram of a food nutrition management system according to a preferred embodiment of the invention.

FIG. 1 is a schematic diagram of a food nutrition management system according to a preferred embodiment of the invention. In FIG. 1, the system includes a portable electronic device 1, a transmitting unit 11, a database 14, an operation unit 13, a code generator 15, an analyzer 16 and a register and management unit 12. The portable electronic device 1 has an input unit 10 and a display unit 17. The input unit 10 receives data and special codes associated with products. The display unit 17 displays a menu and corresponding nutrition component tables. In a preferred embodiment, the portable electronic device 1 is a mobile phone, a personal digital assistant (PDA), a handheld game machine, a laptop/notebook computer, a game host or a network server. The input unit 10 is, for example, keys for inputting data and elements with image input and barcode or code readout functions for reading the special codes associated with products.

The transmitting unit 11 can be a transmitting network for transmitting the data and special codes received by the input unit 10. The data can be one of the personal data, cooking materials, food nutrition component tables and special codes, or their combination. The personal data can be one of the account numbers, passwords, heights, weights, sexes, exercise amounts and, diseases, or their combination. The special codes are 1D, 2D or 3D barcodes, or can be RFID, IC card, etc. As shown in FIG. 1, the database 14 stores nutrition components of the cooking materials, the food nutrition component tables and special codes for the products, restaurant data, and records of personal data and daily nutrition ingestion. In the preferred embodiment, the database 14 is implemented in the mobile phone, personal digital assistant (PDA), handheld game machine, laptop/notebook computer, game host or network server. The restaurant data can be the one of the phone numbers, addresses, open hours and food information, or their combination.

The operation unit 13 accesses the database 14 and accordingly calculates the total nutrition components of a plurality of cooking materials. The code generator 15 generates the special codes of the products. The analyzer 16 extracts the food nutrition component tables from the database 14 for analyzing and comparing them with a suggestion of daily ingestion amounts per person for a variety of nutrition. The register and management unit 12 receives the data and special codes transmitted by the transmitting unit for being recorded. The data received can be one of the account numbers, passwords, heights, weights, sexes, exercise amounts and diseases, or their combination. The special codes are 1D, 2D or 3D barcodes, or can be RFID, IC card, etc.

The food nutrition management system provides the food manufacturers and the restaurants to input the restaurant data, cooking materials or food nutrition component tables, for example, and to accordingly produce the special codes of corresponding products for further providing the information of food nutrition management, or provides the consumers to login for inputting the personal data, cooking materials, food nutrition component tables or special codes or inquiring the nutrition ingestion amounts for a personal food nutrition management.

When the transmitting unit 11 transmits a personal data, the register and management unit 12 stores the personal data and registers it at the database 14. When the transmitting unit 11 transmits cooking materials, the register and management unit 12 extracts the nutrition components of the cooking materials from the database 14 and sends them to the operation unit 13, and the operation unit 13 accordingly calculates the total nutrition components and produces a corresponding food nutrition component table for being stored at the database 14. Accordingly, the code generator 15 can generate a special code for the corresponding food nutrition component table and store it in the database 14. When the transmitting unit 11 transmits a food nutrition component table, the register and management unit 12 stores the food nutrition component table in the database 14 and inquires about whether to generate a corresponding special code through the code generator 15 or not. When generating a corresponding special code is answered, the corresponding special code for a product with the food nutrition component table is generated and stored in the database 14. When the transmitting unit 11 transmits a special code, the register and management unit 12 records the special code, searches the database 14 for the special code, display the food nutrition component table corresponding to the special code on the display unit 17 through the transmitting unit 11.

When the register and management unit 12 receives an inquiry instruction for inquiring nutrition ingestion amounts, the analyzer 16 extracts the food nutrition component tables from the database 14, displays the information of current and past ingestion amounts for a variety of nutrition on the display unit 17, analyzes and compares them with a suggestion of daily ingestion amounts for the variety of nutrition, and accordingly notices the user of which nutrition is insufficient or surplus and of the possible diseases and symptoms corresponding to the nutrition insufficient or surplus.

In a preferred embodiment, the suggestion of daily ingestion amounts per person for the variety of nutrition is produced based on the personal data by the operation unit 13. The personal data can be one of the account numbers, passwords, heights, weights, sexes, exercise amounts and diseases, or their combination. Accordingly, the food nutrition management system can effectively record the daily nutrition ingestion amounts per person, and especially for a patient with one or more special chronic diseases, the daily food content can be controlled easily to thereby achieve the purpose of personal health management.

Figure 2:
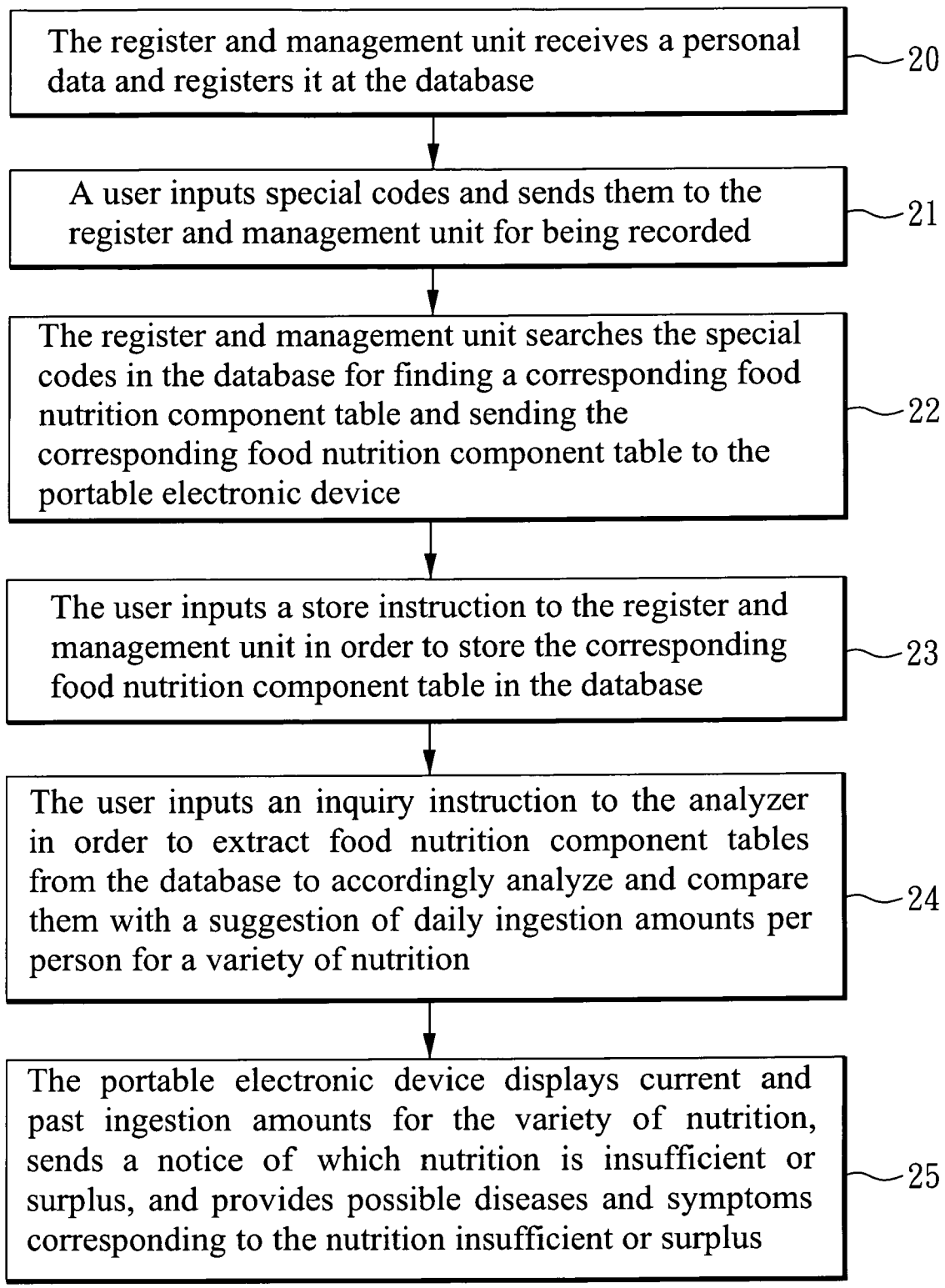
FIG. 2 is a schematic diagram of a food nutrition management method according to a preferred embodiment of the invention.

For further describing and achieving the object, the food nutrition management system is provided with a food nutrition management method. FIG. 2 is a schematic diagram of the food nutrition management method according to a preferred embodiment of the invention. As shown in FIG. 1, the food nutrition management system includes the portable electronic device 1, the transmitting unit 11, the database 14, the operation unit 13, the code generator 15, the analyzer 16 and the register and management unit 12. With reference to FIG. 2, the register and management unit 12 firstly receives a personal data transmitted by the input unit 10 of the portable electronic device 1 through the transmitting unit 11 and registers it at the database 14 (step 20). A user inputs special codes through the input unit 10 and sends them through the transmitting unit 11 to the register and management unit 12 for being recorded (step 21). Namely, the register and management unit 12 records the special codes. Subsequently, the register and management unit 12 searches the special codes in the database 14 for finding a corresponding food nutrition component table and sending the corresponding food nutrition component table through the transmitting unit 11 to the display unit 17 of the portable electronic device 1 for display (step 22). The user inputs a store instruction through the input unit 10, and the register and management unit 12 accordingly stores the corresponding food nutrition component table in the database 14 (step 23). The user inputs an inquiry instruction through the input unit 10, the analyzer 16 accordingly extracts food nutrition component tables from the database for analyzing and comparing them with a suggestion of daily ingestion amounts per person for a variety of nutrition to thereby send a comparison result to the portable electronic device 1 (step 24). Thus, the display unit 17 of the device 1 displays the information of current and past ingestion amounts for the variety of nutrition and notifies the user of which nutrition is insufficient or surplus and of possible diseases and symptoms corresponding to the nutrition insufficient or surplus (step 25).

Although the present invention has been explained in relation to its preferred embodiment, it is to be understood that many other possible modifications and variations can be made without departing from the spirit and scope of the invention as hereinafter claimed.

What is claimed is:

1. A food nutrition management method, which is applied in a food nutrition management system including a portable electronic device, a transmitting unit, a database, an operation unit, a code generator, an analyzer and a register and management unit, the method comprising the steps of:
   (A) receiving a personal data through the transmitting unit from the portable electronic device to the register and management unit, and storing and registering the personal data to the database;
   (B) externally inputting a special code through the portable electronic device, and sending the special code through the transmitting unit to the register and management unit for being recorded;
   (C) using the register and management unit to extract the special code and corresponding food nutrition component table from the database and to send the corresponding food nutrition component table through the transmitting unit to the portable electronic device for display;
   (D) using the register and management unit to store the corresponding food nutrition component table in the database when a store instruction is input through the portable electronic device;
   (E) using the analyzer to extract the corresponding food nutrition component table from the database, compare the corresponding food nutrition component table with a suggestion of daily ingestion amounts per person for a variety of nutrition, and send a comparison result to the portable electronic device when an inquiry instruction is input through the portable electronic device; and
   (F) using the portable electronic device to display current and past ingestion amounts for the variety of nutrition, send a notice of which nutrition is insufficient or surplus, and provide possible diseases and symptoms corresponding to the nutrition insufficient or surplus.

2. The method as claimed in claim 1, wherein the suggestion of daily ingestion amounts per person for the variety of nutrition is calculated and produced based on the personal data by the operation unit.

3. The method as claimed in claim 1, wherein the personal data comprises one or more selected from account numbers, passwords, heights, weights, sexes, exercise amounts and diseases.

4. The method as claimed in claim 1, wherein the special code is one selected from 1D, 2D and 3D barcodes, or is RFID or IC card.

5. The method as claimed in claim 1, wherein the portable electronic device is one selected from mobile phones, personal digital assistants (PDAs), handheld game machines, laptop/notebook computers, game hosts and computers.

6. The method as claimed in claim 1, wherein the portable electronic device comprises an input unit and a display unit.

7. The method as claimed in claim 1, wherein the transmitting unit is a network for data transmission.

8. The method as claimed in claim 1, wherein the database is implemented in a mobile phone, personal digital assistant (PDA), handheld game machine, laptop/notebook computer, game host or network server.

9. A food nutrition management system, comprising:
   a portable electronic device, which has an input unit to receive a data and a special code with product information, and a display unit to display a menu and a food nutrition component table;
   a transmitting unit, which transmits the data and special code received by the input unit;
   a database, which stores nutrition components of a plurality of cooking materials, food nutrition component tables and special codes for a plurality of products, restaurant data, and records of personal data and daily nutrition ingestion;
   an operation unit, which accesses the database and calculates a total of nutrition components of cooking materials;
   a code generator, which produces a special code corresponding to a food nutrition component table;
   an analyzer, which extracts the food nutrition component tables from the database for analyzing and comparing the food nutrition component tables with a suggestion of daily ingestion amounts per person for the variety of nutrition; and
   a register and management unit, which receives the data and special code transmitted by the transmitting unit, wherein, when the data received is a personal data, the register and management unit registers the personal data at the database, and when the inquiry instruction is received by the register and management unit, the register and management unit uses the analyzer to extract the food nutrition component tables from the database in order to accordingly analyze and compare the food nutrition component tables with the suggestion of daily ingestion amounts per person for the variety of nutrition to thereby produce a comparison result, and uses the display unit to display current and past ingestion amounts for the variety of nutrition in order to accord to the comparison result to send a notice of which nutrition is insufficient or surplus and of possible diseases and symptoms corresponding to each nutrition insufficient or surplus.

10. The system as claimed in claim 9, wherein the register and management unit extracts the nutrition components of the plurality of cooking materials from the database when the data transmitted by the transmitting unit is one or more cooking materials, and uses the operation unit to accordingly calculate total nutrition components of the one or more cooking materials, produce the food nutrition component table, store the table in the database, and use the code generator to produce the special code corresponding to the table stored in the database.

11. The system as claimed in claim 9, wherein the register and management unit stores the food nutrition component table in the database and uses the code generator to produce the special code when the data transmitted by the transmitting unit is the food nutrition component table.

12. The system as claimed in claim 9, wherein the register and management unit records the special code with product information, accordingly searches the database, and transmits a food nutrition component table corresponding to the special code with produce information to the display unit for a display when the special code with product information is transmitted by the transmitting unit.

13. The system as claimed in claim 9, wherein the suggestion of daily ingestion amounts per person for the variety of nutrition is calculated and produced based on the personal data by the operation unit.

14. The system as claimed in claim 9, wherein the portable electronic device is one selected from mobile phones, personal digital assistants (PDAs), handheld game machines, laptop/notebook computers, game hosts and computers.

15. The system as claimed in claim 9, wherein the database is implemented in a mobile phone, personal digital assistant (PDA), handheld game machine, laptop/notebook computer, game host or network server.

16. The system as claimed in claim 9, wherein the transmitting unit is a network for data transmission.

17. The system as claimed in claim 9, wherein the personal data comprises one or more selected from account numbers, passwords, heights, weights, sexes, exercise amounts and diseases.

18. The system as claimed in claim 9, wherein the special code is one selected from 1D, 2D and 3D barcodes.

19. The system as claimed in claim 9, wherein the restaurant data is one or more selected from telephones, addresses, open hours and product information.

* * * * *